United States Patent [19]

Anderson, Jr. et al.

[11] Patent Number: 4,936,141

[45] Date of Patent: Jun. 26, 1990

[54] ON-LINE PAPER SHEET STRENGTH DETERMINATION METHOD AND DEVICE

[75] Inventors: Leonard M. Anderson, Jr., San Jose; Lee M. Chase, Los Gatos, both of Calif.

[73] Assignee: Measurex Corporation, Cupertino, Calif.

[21] Appl. No.: 105,635

[22] Filed: Oct. 6, 1987

[51] Int. Cl.$^5$ ............................................. G01N 21/86
[52] U.S. Cl. ..................................... 73/159; 162/198; 356/430; 250/559
[58] Field of Search ................... 73/159; 250/559, 572; 356/429–431; 162/198

[56] References Cited

U.S. PATENT DOCUMENTS 4,644,174  2/1987  Ovellette et al. .................... 250/572
4,648,712  3/1987  Brenholdt ............................ 250/559

OTHER PUBLICATIONS

"Improving the Strength of LinerBoard", R. M. Soszynski, et al., Pulp and Paper Research Institute of Canada, pp. 594–599.

"The Fundamental Properties of Paper Related to its Uses", Transactions of the Symposium at Cambridge: Sep. 1973, edited by Francis Bolam, pp. 60–68.

Primary Examiner—William M. Shoop, Jr.
Assistant Examiner—Brian K. Young
Attorney, Agent, or Firm—Spensley Horn Jubas & Lubitz

[57] ABSTRACT

A method and device for determining the strength of a sheet material, such as paper, utilizing floc size and the variability of the local basis weight of the sheet. The force required to deflect the moving sheet out of a nominal position, the distance the sheet is deflected by said force and the average tension applied to the sheet may also be utilized in the above determination of sheet strength.

27 Claims, 3 Drawing Sheets

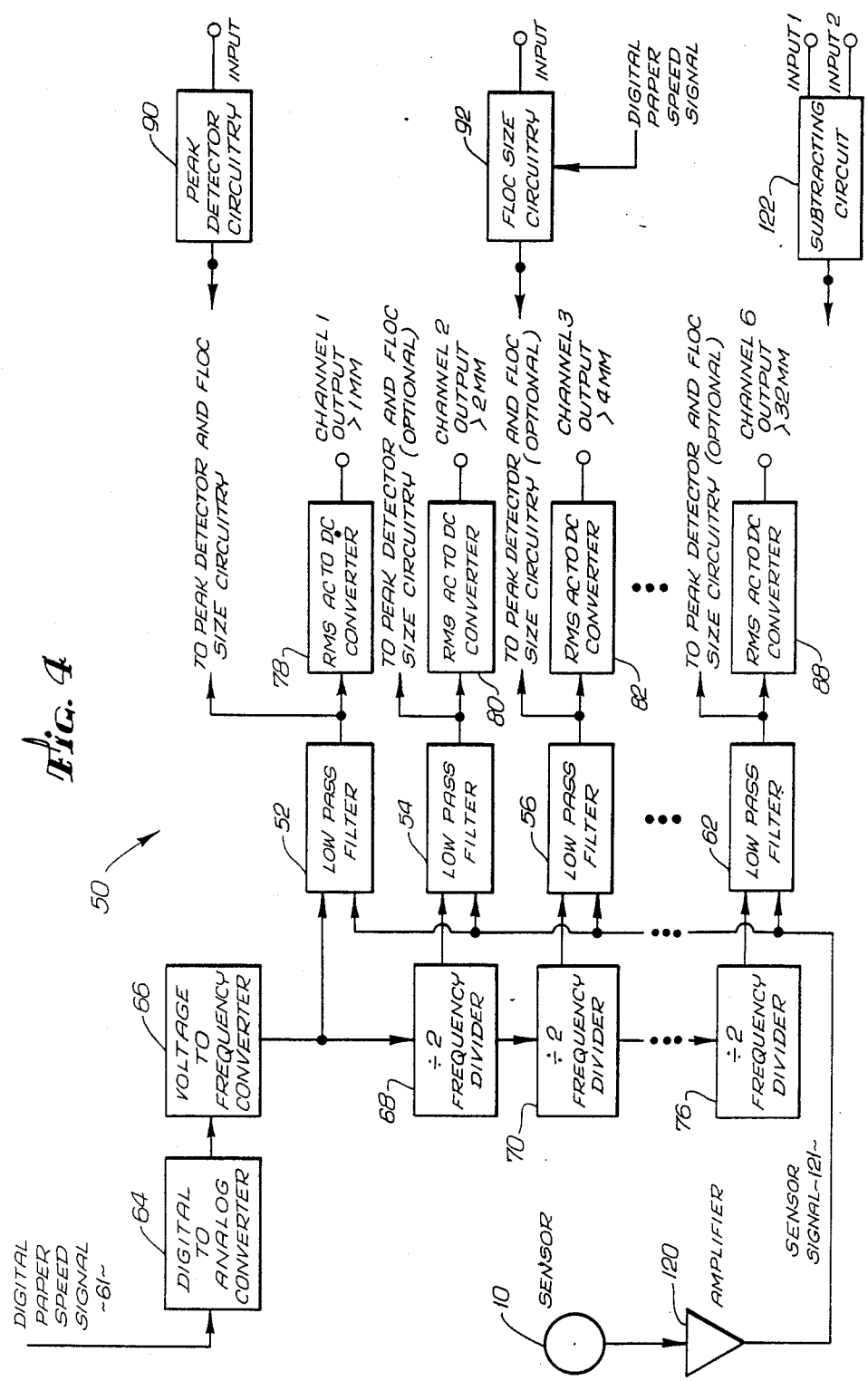

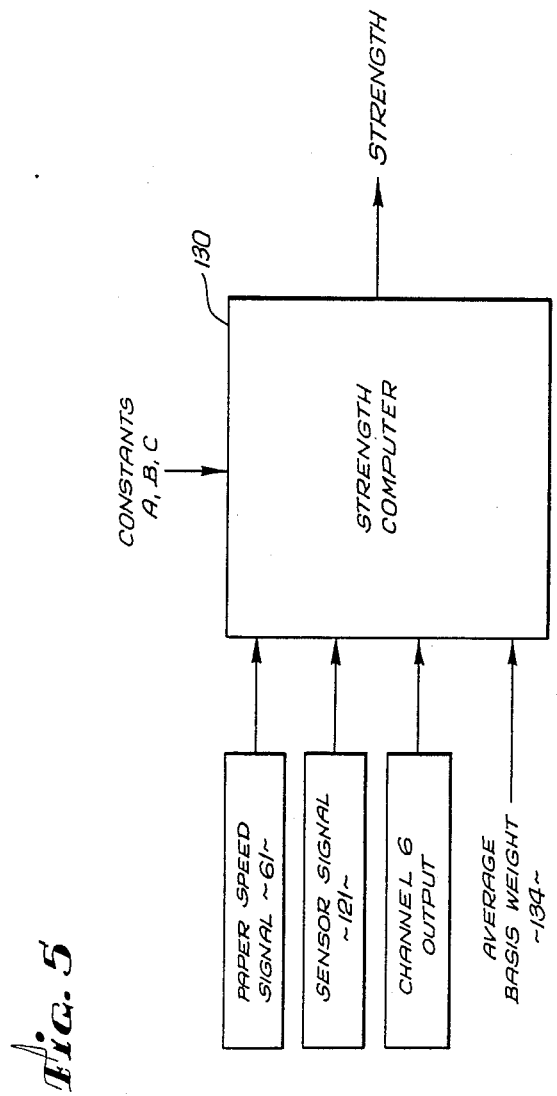

ON-LINE PAPER SHEET STRENGTH DETERMINATION METHOD AND DEVICE

BACKGROUND OF THE INVENTION

This invention relates to a device and method for determination of the strength of a sheet of paper, and more specifically, to a device and method to determine the strength based upon monitoring the variations in the intensity of a narrow beam of light transmitted through the sheet as the sheet moves perpendicularly through the beam.

Paper is produced from a suspension of fibers. These fibers are usually made of cellulose, derived mainly from wood and rags. The evenness of the distribution of these fibers in a sheet of paper is of paramount importance to the optical and printing properties of the sheet. Therefore, one of the chief goals for a paper maker is to develop a paper making process and adjust the parameters of the process to achieve as even a "basis weight" or distribution of these fibers in the finished sheet material as possible. In the paper making art, the term "basis weight" refers to the weight of the paper-forming fibers per unit area of the sheet surface.

Among the critical characteristics of paper and other sheet materials which are important to both manufacturers and users is strength. Many different methods for measuring strength have been proposed in the past, but virtually all suffer from a great disadvantage, namely, the tests are destructive and cannot be used "on line." A number of standardized tests have been devised to provide a basis for specifications by which paper can be bought and sold, and these tests provide arbitrary but nevertheless useful strength indices for comparing the strengths of various papers. Unfortunately, all are destructive, and none can be used "on line." The more common tests are a standardized tensile test, the so-called "STFI" compression test, and the "burst pressure" or "Mullen" test.

In the standard tensile test, a strip of paper is held between two clamps and loaded in tension at a predetermined rate. The loading at failure is taken to be a measure of the tensile strength of the paper. There are a number of standardized procedures which have been adopted to perform this test, e.g., TAPPI Standard T404os-76 and ASTM Standard D828.

The "STFI" compression test for heavy papers is a standardized test whose procedure has been established by the Swedish Technical Forest Institute, as specified by the identifiers: Scan P46 Column 83. In this test a strip of paper to be tested is held between a pair of clamps which are moved together at a fixed rate while the compressive force is monitored. "Rupture" occurs when the compressive force passes a peak and begins to drop. The force at "rupture" is taken as the compressive strength of the paper. Other standard specifications for this test are, e.g., TAPPI 78180s-76 and ASTM D1164.

The strengths of papers as measured by the foregoing tests typically have different values depending on whether the test strip is cut in the machine direction or the cross direction.

A "Mullen" or burst pressure test is conducted by clamping a sample of the paper between two circular clamping rings having a specified standard inside diameter, and building up pressure on one side of the paper until the paper bursts (using a rubber diaphragm and liquid pressure). The pressure required to burst the paper is known as the "burst pressure" and is the figure often used to specify the required strength. Common burst pressure specifications are TAPPI 403os-76 and ASTM D774.

Needless to say, none of these tests lend themselves to use in connection with the continuous measurement of paper strength. Because of their widespread popularity, however, it is desirable that any method used to measure the strength of paper provides results which correlate with one of the recognized standard tests.

In addition to strength, another important paper parameter is the "formation" of the sheet. There is, apparently, no standard definition of "formation." However, for the present purpose "formation" will be defined as the manner in which fibers forming a paper sheet are distributed, disposed and intermixed within the sheet. In all paper sheets, the sheet-forming fibers are, at least to a certain extent, unevenly distributed in bunches called "flocs." However, sheets of paper having generally evenly distributed, intertwined fibers are said to have good formation. Conversely, when the fibers forming the sheet are unacceptably unevenly distributed in flocs, the paper sheet is grainy rather than uniform and is said to have poor formation.

Some researchers have found a correlation between paper formation and strength. However, their research has been limited and primarily theoretical and has not resulted in a device which can be used in practical applications to measure strength of paper being produced on a paper machine. Moreover, although a variety of devices have been tested for measuring paper formation, as will be discussed hereinafter, many are incapable of accurately measuring formation, and none are capable of measuring paper strength.

In one device for measuring formation, called a basis weight sensor (or microdensitometer), a beam of light is transmitted through the sheet as the sheet passes perpendicularly through the beam. The intensity of the beam is measured by a light detector after the beam is transmitted through the paper sheet. This light detector is positioned on the opposite side of the sheet from the light source. The light detector produces an electrical signal indicative of the intensity of the transmitted beam. As the basis weight of the portion of sheet through which the light beam is passing increases, the intensity of the beam transmitted through the sheet decreases. Thus, the electrical signal from the light detector is indicative of the basis weight of the sheet.

As previously mentioned, the fibers forming every sheet of paper tend to congregate in flocs. In any one sheet, these flocs will have a variety of sizes. Thus, as the paper moves perpendicularly through the light beam, the electrical signal produced by the light detector will be modulated at a plurality of frequencies corresponding to the distribution of floc sizes and also to the speed with which the paper sheet moves through the light beam. As the sheet speed increases, the frequency with which the flocs modulate the electrical basis weight signal increases. Similarly, smaller flocs modulate the signal at higher frequencies than larger flocs. The amplitude of these modulations corresponds to the local variations in basis weight or, what amounts to the same thing, the local variations in the distribution of the fibers forming the flocs.

In one technique, the formation characterizing device displays the average peak-to-peak variation in the electrical signal produced by a basis weight sensor. The average peak-to-peak value of the electrical signal is said to indicate the magnitude of variations in the basis weight of the sheet. However, this technique has not been applied to measure strength, and for the reasons discussed below, the technique may give a false indication of the sheet formation.

In many instances, the paper maker will want to make a sheet having as even a fiber distribution as possible, i.e. one having good formation. To accomplish this, the paper maker will want to know, not only the magnitude of the variations in basis weight, but also the size distribution of the flocs. The paper maker will also want to know the strength of the sheet. However, the previously described technique, which yields only the average peak-to-peak value of the basis weight signal, gives no indication of the size of the flocs creating these variations in the basis weight signal or the strength of the sheet.

In another technique for characterizing sheet formation, a beta radiograph is made of a sample sheet of paper. Light is then passed through or reflected off of the radiograph. Variations in the intensity of a narrow beam of this light are converted into an electrical signal as the radiograph moves, at a uniform speed, perpendicularly with respect to the beam. A graphical display is produced of the amplitude of the modulations of this electrical signal as a function of the wavelengths comprising the signal. This display is called a wavelength power spectrum. FIG. 1 illustrates one such display for several grades of paper having good, intermediate and poor formation. This technique has been discussed in great detail by Norman and Wahren in a number papers, including their symposium paper "Mass Distribution and Sheet Properties of Paper."

For some commercial paper manufacturing situations, the Norman and Wahren technique may be inappropriate to measure formation. As illustrated in FIG. 1, at wavelengths below about one millimeter, there is little difference between the wavelength power spectra of a well-formed sheet and a poorly-formed sheet. However, from wavelengths of about one millimeter to thirty-two millimeters, significant differences exist. Thus, the Norman and Wahren technique produces more information than may be necessary for the paper maker to determine formation of a sheet. Another possible disadvantage of this technique is that it provides so much information that its interpretation may be difficult for the non-expert. In many commercial manufacturing situations, the paper maker may prefer a device and technique which provides him or her with only a few numbers, which together completely characterize the formation of the sheet, rather than an entire spectral display. Moreover, this technique, like the previously described technique for measuring the average peak-to-peak value of a basis weight signal, fails to provide the paper maker with an indication of the strength of the sheet.

SUMMARY OF THE INVENTION

The present invention is directed to a method and device which provide a set of electrical output signals indicative of the strength of the sheet. The output signals may be converted into numerical values and displayed to the paper mill operator. The operator can then use these numerical values to monitor the strength of the manufactured sheet and adjust the parameters of the paper making process to achieve a paper sheet having the desired strength. Alternatively, these electrical output signals can be fed into a computer or other device which would then use these output signals to automatically adjust the paper making process to achieve paper having the desired strength.

The device of the present invention includes a basis weight sensor for accurately measuring local variations in the basis weight of a sheet of paper. The sensor includes a light beam source, which is disposed on one side of the sheet, and a "receiver," disposed on the other side of the sheet opposing the light beam source. The receiver includes a light pipe, such as a narrow sapphire rod. One end of the rod abuts against the sheet on the opposite side of the sheet from the light source. As the sheet passes through the sensor perpendicular to the light beam, the sheet is held against the end of the rod so that only light which passes through the sheet can enter the rod. This rod directs at least a portion of the light beam to a light detecting device such as a photodiode. The photodiode then produces an electrical output proportional to the intensity of the light beam after the beam is transmitted through the sheet.

As the sheet of paper passes through the basis weight sensor, local variations in the basis weight of the sheet create variations in the intensity of the light beam transmitted through the sheet. The light detecting device in the receiver portion of the sensor produces an electrical signal proportional to the intensity of the transmitted beam and hence inversely proportional to the basis weight of the portion of the sheet through which the detected portion of the beam is passing. Because paper consists of flocs of a variety of sizes, the electrical signal from the sensor is modulated at number of frequencies as the paper sheet passes between the light source and receiver halves of the sensor. These frequencies are dependent upon both the speed with which the paper passes through the sensor and the size of the various flocs forming the sheet. However, the signal processing circuits of the present invention account for changes in the speed with which the paper passes through the sensor. Thus, the output signals characterizing formation are independent of the paper speed.

It should be understood that the basis weight sensor described above may not measure exactly the same "basis weight" as is measured by a conventional nuclear basis weight gauge. The basis weight sensor taught herein is based upon optical transmittance of the paper sheet which may vary with wood fiber type, paper additives or other factors, which do not affect the "basis weight" measured by a nuclear basis weight gauge. However, for the purposes of this application, the present gauge will be said to measure basis weight or local basis weight, whereas a conventional nuclear gauge will be said to measure average basis weight.

The signal processing circuitry of the present invention has a plurality of electrical channels. Each channel processes basis weight signals from the basis weight sensor corresponding to a different predetermined minimum floc size, the floc sizes larger than that minimum. This is accomplished by placing a low pass filter at the input end of each channel. The signal from the basis weight sensor is fed into each of these low pass filters. However, the low pass filter of each succeeding channel has a cutoff frequency lower than that of the low pass filter in the preceding channel. In addition, the cutoff frequency for each of these low pass filters is variable and is controlled to be proportional to the speed with which the paper passes through the sensor. Thus, the cutoff frequency for the low pass filter of each channel corresponds to flocs of a particular predetermined minimum size and continues to correspond to flocs of this predetermined minimum size even when the speed with which the paper moves through the sensor is changed.

The output of each low pass filter is directed to a separate AC to DC converting circuit which converts the filtered signal from the associated low pass filter to a DC output proportional to the root-mean-square (hereafter "RMS") value of the signal from the low pass filter. The output of each AC to DC converter therefore indicates the magnitude of the variations in the basis weight of the sheet created by flocs of a certain minimum size (i.e. the flocs modulating the basis weight signal at a frequency just below the cut-off frequency) and all flocs larger than that minimum size.

Additionally, the signal from the low pass filter of the first channel (the first channel low pass filter has the highest cutoff frequency) can be directed to a peak detector circuit. This circuit can be made to indicate the maximum intensity of the basis weight signal over a predetermined length of paper which passes through the basis weight sensor or the average of several signal peaks. A more intense transmitted light beam corresponds to a lower basis weight. Therefore, when the peak detector is made to indicate the maximum intensity of the basis weight signal, the magnitude of the output of the peak detector circuit characterizes the strength of weakest point of the sheet. Alternatively, when the peak detector circuit is made to indicate the average of several signal peaks, then the output of this circuit characterizes an average of the strengths of several of the weakest points in the sheet.

Although the strength of the sheet at its weakest point may be useful to the papermaker, of more importance may be the overall strength. To determine the overall strength additional information is necessary. In particular, the average basis weight of the sheet is determined with a conventional nuclear gauge, and the transmission of the sheet is determined with the local basis weight sensor and the line speed of the paper machine must be determined by conventional means. Once this data is available, it is utilized along with other data from the local basis weight sensor to determine sheet strength.

BRIEF DESCRIPTION OF THE DRAWINGS

FIG. 4 illustrates a block diagram of one embodiment of the circuitry of the present invention used to process signals from the basis weight sensor of FIG. 2.

FIG. 5 illustrates a block diagram of one embodiment of a computer system to utilize signals from the circuitry of FIG. 4.

DETAILED DESCRIPTION OF THE PREFERRED EMBODIMENT

A. The Basis Weight Sensor

Figure 2:
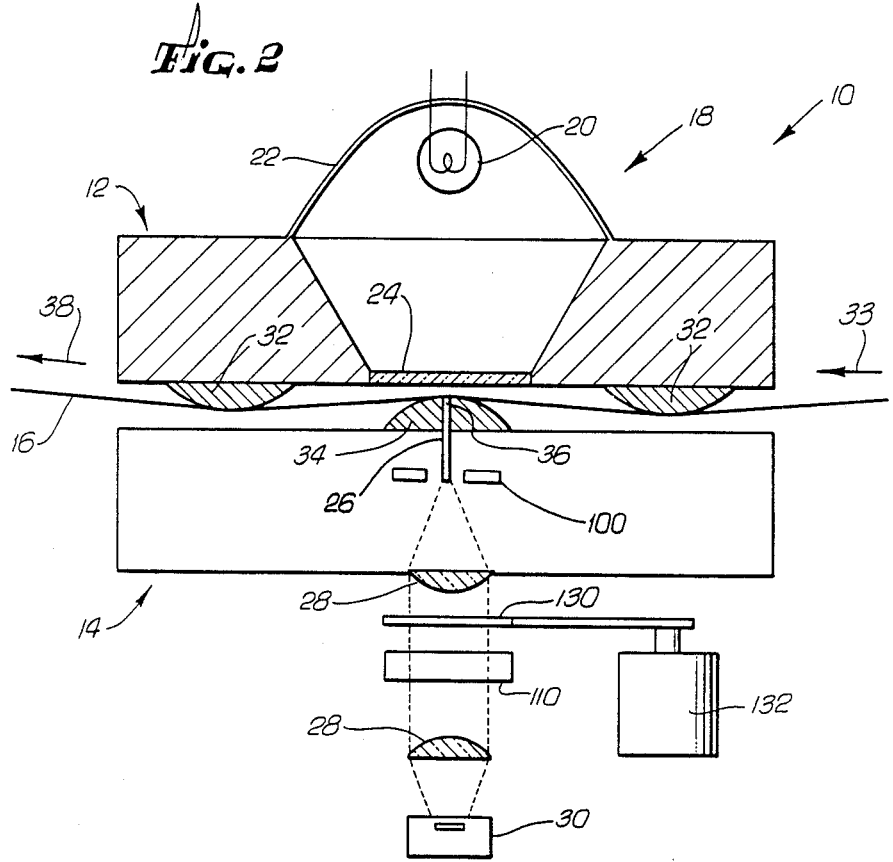
FIG. 2 illustrates one embodiment of the basis weight sensor of the present invention.

FIG. 2 illustrates a presently preferred embodiment of the basis weight sensor 10 of the present invention. This sensor 10 can be considered as consisting of two halves, a "source" half 12 and a "receiver" half 14. The source half 12, disposed on one side of the sheet of paper 16, directs a beam of light through the sheet 16 whose formation is to be determined. The receiver half 14 is disposed on the opposite side of the sheet 16 and produces an electrical signal proportional to the intensity of the light which is transmitted through the sheet 16. The source half 12 includes a light source 18, such as a high intensity incandescent lamp 20, and a reflector 22 for directing the beam of light from the lamp 20 toward the sheet 16. As the light travels toward the sheet 16, it passes through a diffuser 24 which randomizes the direction of the photons as the beam passes through it. It is important to use a diffuse source of light. If a non-diffuse source of light is used, the receiver half 14 of the sensor 10 may measure variations in the intensity of the transmitted beam caused by variations in the reflectance of the sheet surface to light coming from one particular direction, rather than variations in transmitted light intensity caused by local variations in basis weight of the sheet 16.

The receiver half 14 of the sensor 10 includes a 1 mm. diameter sapphire light pipe 26 for directing a small spot of the diffuse light beam which is transmitted through the sheet 16 toward a lens system 28. This lens system 28 focuses the light from the light pipe 26 onto a light sensitive silicon photodiode 30. The photodiode 30 produces an electrical output signal proportional to the intensity of the spot of transmitted light. Thus it can be seen that the sensor 10 measures the basis weight of a 1 mm diameter circle of paper.

It is important that the sheet 16 be held firmly against the end of the light pipe 36 as the sheet passes through the sensor 10 so that any light impinging upon the end of the light pipe 36 must have traveled through the sheet 16. To accomplish this goal, the source half 12 of the formation sensor 10 is formed with protrusions 32, called "skid plates," on opposite sides of the light pipe 26. In addition, the end of the light pipe 36 extends toward the sheet 16 and is protected by another skid plate 34 surrounding the light pipe 26 such that the paper sheet 16, travelling in the direction of the arrows 38 between the source and receiver halves of the sensor 10, is held by the skid plates 32, 34 against the end of the light pipe 36.

As the paper sheet 16 passes between and rubs against the skid plates 32, 34 and the end of the light pipe 36, the paper will tend to wear away the skid plates and the end of the light pipe 36. The skid plates 32, 34 are therefore constructed of an abrasion resistant material such as steel alloys and the light pipe 26 is made of sapphire or some other similarly transparent but abrasion resistant material.

B. The Signal Processing Circuitry

As previously mentioned, the basis weight sensor 10 produces an electrical signal the magnitude of which is inversely proportional to the basis weight of the portion of the sheet 16 through which the detected spot of the light beam is transmitted. The sheet 16 is formed from flocs so that the transmitted beam intensity, and hence the sensor signal, varies as the paper sheet 16 passes through the sensor 10. The sensor signal is then amplified by amplifier 120 and the amplified sensor signal 121 is fed to the signal processing circuitry. The sensor signal 121 is indicative of the local basis weight of that portion of the sheet contacting the end of the light pipe 36, i.e. a 1 mm diameter circle.

A presently preferred embodiment of the signal processing circuitry 50 is shown in block diagram form in FIG. 4. This signal processing circuitry 50 comprises a plurality of low pass filters 52-62. Each filter 52-62 is associated with a particular electrical "channel." Each channel includes one of these low pass filters 52-62 and an RMS-AC to DC converter 78-88. The device of the present invention may have any number of channels (channels 4-5 are omitted to simplify the figure). In the embodiment of FIG. 4, the device has six channels. Each of the six low pass filters 52-62 receives two input signals. The first input signal to each of the low pass filters 52-62 comes from the previously described basis weight sensor 10. This signal is directed to the first input of each low pass filter 52-62.

The cutoff frequency for each low pass filter 52-62 is proportional to the frequency of a second input signal. The frequency of the second input signal is not the same for each low pass filter 52-62. Instead, the frequency of the second input to each low pass filter 52-62 is one-half of the frequency of the signal fed to the second input of the low pass filter of the preceding channel. Thus, the cutoff frequency of the first channel low pass filter is highest and the cutoff frequency of the sixth channel low pass filter 62 is lower than the cutoff frequency of any of the other low pass filters 52-62. In other words, the first channel low pass filter 52 passes a signal from the basis weight sensor 10 the highest frequency component of which corresponds to a certain minimum floc size. The sensor 10 cannot sense changes in basis weight that occur in less than 1 mm since the light pipe 26 (FIG. 2) of the basis weight sensor 10 has a 1 mm. diameter. Thus, the highest frequency basis weight signal sent the low pass filters corresponds to 1 mm. flocs. Therefore, in the present embodiment, the frequency of the signal sent to the second input of the low pass filter 52 of channel 1 is adjusted so that this low pass filter 52 has a cutoff frequency corresponding to variations in the basis weight caused by 1 mm. flocs. The frequency of the signal sent to the second inputs of the low pass filters 54-62 of channels 2-6 is adjusted so that the cutoff frequencies of these low pass filters 54-62 correspond to floc sizes of 2 mm, 4 mm, 8 mm, 16 mm and 32 mm, respectively. The frequency of the second input to each low pass filter 52-62 is also proportional to the speed with which the paper passes through the sensor 10. Thus, the cutoff frequency of each low pass filter 52-62 continues to correspond to a basis weight signal frequency characteristic of flocs of the above-mentioned sizes, even when of the speed with which the paper sheet passes through the sensor 10 changes.

In the present preferred embodiment, the second input signal to each low pass filter 52-62 is derived by first measuring the speed with which the paper sheet passes through the sensor 10. Devices which measure the speed of a paper sheet are well known in the art. Many modern paper mills are highly automated and include a computer which monitors and controls various parameters of the paper making process. Thus, in the present preferred embodiment, a digital paper speed signal 61 from the mill's computer indicative of the paper speed is conveniently used to control the cutoff frequency of the low pass filter 52-62 of each channel. This digital speed signal 61 is directed to a digital to analog converter 64 which receives the digital speed signal and outputs a voltage proportional to the paper speed. This voltage is then input to a voltage to frequency converter 66 (hereinafter "VFC"). The VFC 66 then outputs a signal having a frequency which is proportional to the output voltage of the digital to analog converter 64 and hence to speed of the paper passing through the sensor 10. Each channel, except the first channel, includes a frequency divider 68-76. The signal from the VFC 66 is fed directly into the second input of the first channel low pass filter 52, and also into the frequency divider 68 of the second channel. The frequency divider 68 of the second channel divides the frequency of the signal received from the VFC 66 and the resulting lower frequency divider 70 of the third channel. Thus, the second input to the low pass filter 52 of the first channel is at frequency X. Frequency X corresponds to the speed with which the paper passes through the sensor 10. Since divide-by-two frequency dividers are used in the present preferred embodiment, the frequency input to the low pass filter 54 of the second channel is at frequency X/2. The signal output by frequency divider 68 of the second channel is also fed the input of the frequency divider 70 of the third channel. Each succeeding channel 4 and 5 also have frequency dividers, for example frequency divider 76, which receive the signal from the frequency divider of the preceding channel and output a signal at one-half the frequency of the received signal. Thus, the frequency of the signal fed to the second input of the low pass filter 56 of the third channel is at frequency X/4, the frequency of the signal fed to the second input of the fourth channel low pass filter (not shown) is X/8, etc. In this way, the output of the low pass filter 52 of the first channel comprises frequencies corresponding to floc sizes greater than or equal to a minimum size, i.e. 1 mm. The highest frequency passes through to the output of the low pass filter in each succeeding channel corresponds to floc sizes of increasingly larger minimum size, i.e. 2 mm, 4 mm, 8 mm, 16 mm and 32 mm. The output of each channel's low pass filter 52-62 is then processed to indicate various formation parameters of the sheet being sensed for floc sizes at and above the minimum floc size for the particular channel.

To derive an output signal indicative of the magnitude of the variations in the basis weight of the sheet, the output of each low pass filter 52-62 is directed to an associated AC to DC converter 78-88. Each AC to DC converter 78-88 produces a DC voltage equivalent to the RMS value of the AC signal output from the associated low pass filter 52-62. The RMS value of the DC voltage produced by each AC to DC converter 78-88 is proportional to the magnitude of variation in the basis weight of the sheet caused by flocs of a particular minimum size. Since the cutoff frequency of the low pass filters 52-62 in each succeeding channel is set to succeedingly lower frequencies, the magnitude of the RMS DC output voltage of each succeeding channel corresponds to the magnitude of variation in the basis weight of the sheet caused by succeedingly larger minimum floc sizes.

In certain situations, the mill operator will want to know the magnitude of the basis weight variations in the sheet caused by flocs in a particular size range. The device of the present invention can provide this information by simply subtracting the RMS DC output of the AC to DC converter of one channel from the RMS DC output of the AC to DC converter of another channel. The difference between the value of these outputs corresponds to the magnitude of the basis weight variations caused by flocs in the size range between the cutoff frequencies of the low pass filters of the two channels.

A subtracting circuit 122 may be provided to receive, at inputs 1 and 2, the outputs of any two selected AC to DC converters. This subtracting circuit produces an output voltage corresponding to the difference between the outputs of the two selected AC to DC converters. Alternatively, if the output of the various AC to DC converters are numerically displayed, then the paper mill operator can obtain the difference between any two such outputs by subtraction. For example, to determine the magnitude of the basis weight variations caused by flocs between 4 mm and 8 mm, the paper mill operator simply subtracts the value of the output of the fourth channel AC to DC converter from the value of the output of the third channel AC to DC converter.

Many standard "RMS" AC to DC converters actually measure the peak-to-peak voltage of the incoming signal and then provide an output DC signal which corresponds to the true RMS value of the input signal only if the input signal is sinusoidal. However, the basis weight signal waveshape is generally not sinusoidal. It is, therefore, usually important that the AC to DC converters 78–88 of the present invention output a DC voltage corresponding to the true RMS value of the basis weight signal, otherwise the output signal of these AC to DC converters 78–88 may provide an inaccurate measure of the basis weight variations.

The use of true RMS-AC to DC converters is particularly important when the output of the converter of one channel is subtracted from the output of a converter of another channel to thereby determine the contribution to the basis weight variations caused by flocs in a particular size range. Flocs of different sizes may cause the same peak-to-peak changes in the basis weight signal, even though their contribution to the RMS value of the basis weight signal is different. Thus, subtracting an AC to DC converter output derived from a basis weight signal containing frequencies corresponding to 4 mm. minimum floc sizes, should and would yield a signal indicative of the contribution to basis weight variation caused by flocs in the 4–8 mm size range, if true RMS AC to DC converters are used. However, if the "RMS" signal is actually derived from a measurement of the peak-to-peak signal value, the flocs of different sizes are causing the same peak-to-peak change in basis weight signal, then the difference between the outputs of the two AC to DC converters would be zero. However, this would not be a correct indication of the contribution to basis weight variation caused by the flocs in the 4–8 mm range. Thus, the use of standard peak-to-peak AC to DC converters may give false readings when used in the device of the present invention.

Another parameter, indicative of the strength of the weakest portion of the sheet, is obtained by feeding the output of the low pass filter 52 of the first channel to the input of a peak detecting circuit 90. Since, as previously mentioned, the magnitude of the intensity of the transmitted beam is inversely proportional to the basis weight of the sheet, the magnitude of the AC signal at the output of this low pass filter 52 will also be inversely proportional to the local basis weight of the portion of the sheet then being sensed by the sensor 10. The peak detecting circuit 90 may be designed to provide a DC output proportional to the largest voltage peak which passes through the first channel low pass filter 52 in a predetermined time period or for a predetermined length of sheet passing through the sensor 10. The magnitude of this signal indicates the weakest point in the sheet. Alternatively, the peak detector circuit 10 may also be designed to produce an output proportional to the average of several signal peaks over a set period of time or length of sheet passing through the sensor 10. In this latter case, the output of the peak detector circuit 90 would characterize an average weak spot in the sheet.

The signal processing circuits 50 of the present invention may provide the paper manufacturer with yet another output signal indicative of another characteristic of the paper sheet—the average floc size. To obtain this parameter, the output of the low pass filter 52 of the first channel is fed to a floc size measuring circuit 92. This circuit 92 counts the number of times, during a predetermined time interval, that the output signal from the low pass filter 52 of the first channel achieves a value corresponding to the average of the output signal. (This can be called "crossings" i.e. the rate at which the signal from filter 52 "crosses" the average of the signal.) The frequency of crossings divided by the speed of the paper through the sensor indicates the average size of the flocs forming the sheet. A floc size measuring circuit, not shown, performs this division and outputs a signal corresponding to the average floc size. For example, if the paper sheet is moving at 1000 m/min and the output from the low pass filter of the first channel achieved a value corresponding to the average of the output 3333 times in a one second time interval, then the average floc size of the sheet is 10 mm (1000 m/min ·1 min/60 sec·1 sec/3333 crossings ·2 crossings/floc). Thus, by sensing the local basis weight of the paper sheet along a line or curve (hereinafter collectively "line") along the sheet surface, the device and method of the present invention can provide the paper manufacturer with an output signal indicative of the size of the flocs forming the sheet.

C. Use and Calibration of the Basis Weight Sensor

In a paper mill, paper is typically produced in sheets about 25 feet wide. To characterize the entire sheet, one basis weight formation sensor can be moved or "scanned" back and forth in the "cross direction" of the sheet (i.e. across the width of the sheet) as the sheet moves along in the "machine direction" (i.e. the lengthwise direction). Alternatively, a plurality of sensors can be scanned back and forth in the cross direction across only a part of the width of the sheet. If, for example, 50 basis weight sensors are used on a 25 foot wide sheet, then each sensor would be made to scan back and forth across a 6 inch wide strip of the sheet. Typically, paper mills produce such sheets at about more than 1000 feet per minute and the back and forth scanning speed of the sensor in the present embodiment may be set at 60 feet per minute. Thus, the cutoff frequency of the low pass filters may be made proportional only to the speed with which the sheet moves in the machine direction without introducing substantial error into the output readings. The additional contribution to the speed with which the paper moves through the sensor, caused by the cross directional movement of the sensor, is minimal, and can usually be ignored.

For the receiver part of the basis weight sensor 14 (FIG. 2) to operate properly, the light from the source side of the sensor 12 must be aligned directly opposite the sheet from the receiver 14. However, the two halves of the basis weight sensor 10 cannot be directly connected together since the paper sheet 16 passes between these two halves. A number of different mechanisms can be used to keep the two halves of the sensor 10 directly opposite to each other as they scan back and forth across the sheet 16. One such device, for example, consists of two tracks (not shown), one on each side of the sheet 16. The source side of the sensor 12 rides on one of the tracks and the receiver side of the sensor 14 rides on the other track. A gear or pulley system moves the two halves of the sensor in unison and opposite each other back and forth across the width of the sheet 16. In this way, the source 12 and receiver 14 halves remain directly opposite each other without the necessity of penetrating the sheet with a connecting member.

Figure 1:
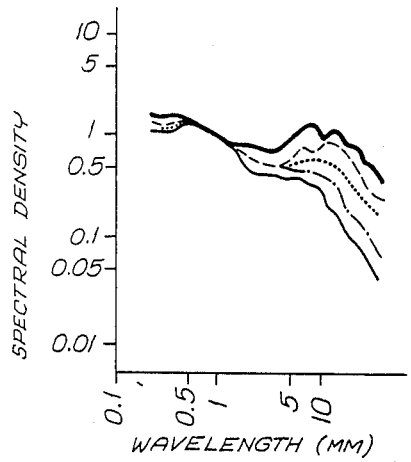
FIG. 1 illustrates wavelength power spectra for several different grades of paper.
Figure 3:
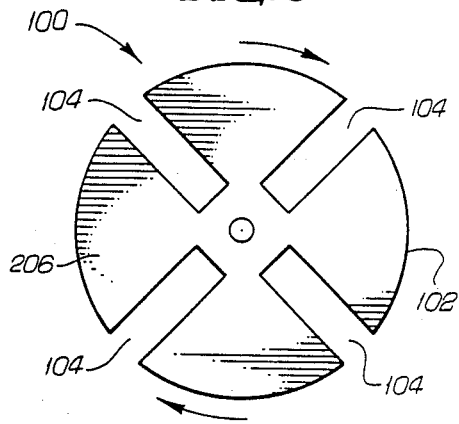
FIG. 3 illustrates a chopper wheel for calibrating the device of the present invention.

Calibration of the basis weight sensor 10 may be done "off sheet", i.e. without having a paper sheet between the two sensor halves. To calibrate the outputs of the low pass filters, a chopper wheel 100 (FIGS. 2-3) is positioned between the sensor's light source 18 and photodiode 30. In the present embodiment, the chopper wheel 100 is positioned at the base of the light pipe 26. The chopper wheel 100 is made from a circular disc 102 of opaque material having a plurality of radial slots 104 positioned around the wheel 100. The chopper wheel 100 is driven at a known rotational speed so that the photodiode 30 receives pulses of light. The pulsing rate is determined by the predetermined speed of rotation of the wheel 100. The paper speed signal can then be set so that the low pass filters of all channels 52-62 (FIG. 4) will transmit signals to the associated RMS-AC to DC converters 78-88. Then, by inputting successively lower paper speeds, the low pass filter cutoff frequencies can be calibrated. For example, if a chopper wheel 100 with four radial slots 104, like that of FIG. 3, is rotated at a speed of 142.5 rotations per second, the chopper wheel 100 will modulate the light impinging upon the light detector at 570 Hz. If the paper speed signal from the VFC 66 is faster than 1094 m/min., then all channels will see the signal. However, as the paper speed drops below 1094 m/min., only channels 1-5 will provide an output. Further decreases in the paper speed signal will cause additional low pass filters to cutoff the signal from the basis weight sensor 10.

Any device which modulates the intensity of the light reaching the light detector can be used other than a chopper wheel 100. For example, a tuning fork, the arms of which oscillate into and out of the light beam at a known frequency, could be used in place of a chopper wheel 100.

Additional information is generated using the data produced with the basis weight sensor 10 in the "off sheet" position and the chopper wheel 100 operating. In particular, sensor signal 121 from amplifier 120 is averaged over a predetermined time interval. This signal is divided by the value of this same signal 121 during the "offsheet" condition of the sensor 10 and the resulting value, T, indicates the average transmittance of the paper. The average transmittance, T, is used as a corrector, as discussed below, for the effects of long term variations in paper color or transmittance, which may occur as the wood fiber type, digester chemistry or additives are varied.

Different types of paper will preferentially absorb or reflect certain frequencies of light. Therefore, to optimize the sensitivity of the basis weight sensor to changes in basis weight, an optical band pass filter 110 (FIG. 2) may be placed in the path of the light beam. This band pass filter 110 will preferentially pass light of certain frequencies to the photodiode 30.

To properly measure variations in the basis weight of the sheet, it is important that the amplified sensor signal 121 from amplifier 120 (FIG. 4) be inversely proportional to the basis weight of the sheet. To ensure that the amplitude of the sensor signal 121 fed to the low pass filters 52-62 responds linearly to changes in basis weight, the amplified sensor signal can be measured with and without a neutral density filter 130 (FIG. 2) placed in the path of the light beam. The neutral density filter 130 attenuates the beam intensity by a known percentage. The amplitude of the amplified sensor signal 121 should be measured first while the pivot 132 has pivoted the neutral density filter 130 out of the path of the beam. Then, the neutral density filter 130 is pivoted, by the pivot 132, into the path of the beam. While the neutral density filter 130 is in the beam path, the amplified basis weight signal should again be measured. Non-linearities in the output of the sensor can then be compensated for by adjusting the amplifier (FIG. 4) so that the change in the amplitude of the amplified basis weight signal caused by placing the neutral density filter 130 in the beam path linearly corresponds to the known change in the light beam intensity caused by positioning the neutral density filter 130 in the beam path.

D. Determination of Strength

FIG. 5 illustrates the present computer system for determining paper strength. The strength computer 130 can be a stand-alone computer or it can be a software program running on a computer which runs other programs as well. The computer 130 receives: (i) the digital paper speed signal 61; (ii) the sensor signal 121 from the amplifier 120; (iii) the output of channel 6 from RMS AC to DC converter 88; (iv) the signal from floc size circuit 92; and (v) the average basis weight signal 134 from a nuclear basis weight gauge, not shown. The nuclear basis weight gauge is a conventional gauge e.g. according to U.S. Pat. No. 3,757,122. Also, constants are entered into the computer 130. Based upon this data, the computer 130 determines the strength of the sheet as discussed below.

According to the present embodiment the computer utilizes the following algorithm to determine strength:

$$S = A + B^*ABW + C^*ABW\left[\frac{CROSS}{T^*SP}\right] + D\left[\frac{RMS_{32}}{T}\right] \quad (1)$$

Where:
S = Mullen strength
$RMS_{32}$ = Channel 6 output from RMS AC to DC converter 88 (>32 mm)
ABW = average basis weight signal 134
T = transmittance
SP = paper speed 61
A, B, C and D are constants
Cross = output of circuit 92 (i.e. crossings)

The transmittance, T, is determined according to the formula:

$$T = \frac{A_{ol}}{A_{os}} \quad (2)$$

Where:
$A_{ol}$ = signal 121 while the sensor 10 is measuring the sheet of paper (on line)
$A_{os}$ = signal 121 while the sensor 10 is "off sheet" during calibration.

As an example of the application of our equation(1) in the determination of Mullen strength for 42 to 69 pound liner board, equation (1) results in good correlation with laboratory measurements. In this example, we found that using $RMS_{32}$, the output of channel 6 of circuit 50, achieved better results than using the output of any of the other channels 1-5. However, in some cases the use of the output of another channel may lead to better results, and in some cases, it may be preferable to modify the circuit 50 to add a channel which measures only flocs with a minimum size greater than 32 mm and use the signal related to such larger floc size.

In this example, the units of measurement were as follows:
  $RMS_{32}$ is dimensionless
  ABW is in pounds/1000 ft$^2$
  T is dimensionless
  SP is in feet/minute In this example, our constants were determined by linear regression and were:
  A=99.4
  B=0.419
  C=0.113
  D=−177

In practice, the constants A, B, C and D should be determined before the present system is used for actual measurement or control. This is done by operating the present device to measure a sheet and analyzing a portion of the same sheet in a laboratory using a conventional laboratory method. Then the constants are calculated by linear regression of the laboratory data with respect to data from the present system.

It should be understood that equation (1) can be modified in a number of ways and still be used to determine strength. For example, as discussed above, S=Mullen strength; however, other strength parameters such as tensile strength, STFI, etc. can be determined by choosing the constants A, B, C and D (and in some cases other parameters) appropriately.

It should also be understood that equation (1) is a member of a class of formulas which could be used to operate on local basis weight and floc size data to determine paper strength.

The expression CROSS/T*SP is inversely proportional to the floc size. Larger floc sizes usually result in weaker paper. The expression, $RMS_{32}/T$ is proportional to the variability of local basis weight across the sheet. Large variability in local basis weight indicates local basis weight regions which are likely to be weak. (Thus, the coefficient D in equation (1) is negative.) Thus, we have found a method to determine the strength of a moving sheet of paper based upon the floc size and variability of the local basis weight of the sheet.

In some applications equation (1) can be modified to provide greater accuracy. For example, in some cases we can determine strength as follows:

$$S = A + B^*ABW + X^*\frac{CROSS}{T^*SP} + Y^*\frac{RMS_{32}}{T} + \qquad (3)$$
$$E\frac{La + Lc}{(C + Z)^*(T + F)} + F\frac{Lb + Ld}{(D + Z)^*(T + G)}$$

Where:
  (i) the parameters in equation (3) are the same as those in equation (1) with the same labels;
  (ii) A, B, X, Y, E and F are constants;
  (iii) La, Lb, Lc and Ld and C, D, F, G, Z and T are all defined in patent application serial number 920,107 filed Oct. 16, 1986 titled "System and Method for the Determination of the Strength of Sheet Materials." Said application is incorporated herein by this reference.

One preferred embodiment of the present invention has been described. Nevertheless, it will be understood that various modifications may be made to the system described herein without departing from the spirit and scope of the invention. Moreover, sheet materials other than paper may be passed through the sensor and characterized by the device of the present invention. Thus, the present inventions is not limited to the preferred embodiments described herein, nor is it limited strictly to use with paper.

We claim:

1. A method for determining the strength of a moving sheet of paper comprising the steps of:
   (a) measuring the average basis weight of the sheet;
   (b) measuring the local basis weight of the sheet;
   (c) measuring the transmittance of the sheet;
   (d) measuring the line speed of the sheet;
   (e) measuring a parameter indicative of the floc size of the sheet; and
   (f) determining the strength of the sheet based upon the average basis weight, the local basis weight, the transmittance, the parameter indicative of the floc size and the line speed.

2. A method for determining the strength of a sheet of paper comprising the steps of:
   (a) measuring the variability of the local basis weight of the sheet;
   (b) measuring a parameter indicative of the floc size of the sheet; and
   (c) determining the strength of the sheet based upon the variability of the local basis weight and the parameter indicative of the floc size of the sheet.

3. The method of claim 1, wherein the measurement of the local basis weight includes a measurement of the variability of the local basis weight restricted to variations caused by flocs greater than about 32 mm.

4. The method of claim 1, wherein the measurement of the local basis weight includes a measurement of the variability of the local basis weight restricted to variations caused by flocs greater than about 16 mm.

5. The method of claim 1, wherein the measurement of the local basis weight includes a measurement of the variability of the local basis weight restricted to variations caused by flocs greater than about 8 mm.

6. The method of claim 1, wherein the measurement of the local basis weight includes a measurement of the variability of the local basis weight restricted to variations caused by flocs greater than about 4 mm.

7. The method of claim 1, wherein the measurement of the local basis weight includes a measurement of the variability of the local basis weight restricted to variations caused by flocs greater than a predetermined size.

8. The method of claim 2, wherein the measurement of the variability of the local basis weight of the sheet includes a measurement restricted to the variability in basis weight caused by flocs greater than about 32 mm.

9. The method of claim 2, wherein the measurement of the variability of the local basis weight of the sheet includes a measurement restricted to the variability in basis weight caused by flocs greater than about 16 mm.

10. The method of claim 2, wherein the measurement of the variability of the local basis weight of the sheet includes a measurement restricted to the variability in basis weight caused by flocs greater than about 8 mm.

11. The method of claim 2, wherein the measurement of the variability of the local basis weight of the sheet includes a measurement restricted to the variability in basis weight caused by flocs greater than about 4 mm.

12. The method of claim 2, wherein the measurement of the variability of the local basis weight of the sheet includes a measurement restricted to the variability in basis weight caused by flocs greater than a predetermined size.

13. The method of claim 2, further comprising the step of measuring the average basis weight of the sheet, wherein the determination of the strength of the sheet is based upon the average basis weight measurement in addition to the variability of the local basis weight and the floc size.

14. A device for determining the strength of a sheet of material, comprising:
   means for measuring the variability of the local basis weight of the sheet and for generating a first signal indicative of the measured variability;
   means for measuring a parameter indicative of the floc size of the sheet, and for generating a second signal indicative of the measured parameter; and
   a computer, operatively coupled to the means for measuring the variability of the local basis weight and the means for measuring the parameter indicative of floc size, to receive the first and second signals and compute the strength of the sheet based upon the first and second signals.

15. The device of claim 14, further comprising an average basis weight sensor for sensing the average basis weight of the sheet, wherein the sensor generates a third signal indicative of the sensed average basis weight, the computer being operatively coupled to the average basis weight sensor to receive the third signal and programmed to compute the strength of the sheet based upon the third signal in addition to the first and second signals.

16. The device of claim 14, wherein the first signal is indicative of the variability of the local basis weight caused by flocs greater than about 32 mm.

17. The device of claim 14, wherein the first signal is indicative of the variability of the local basis weight caused by flocs greater than about 16 mm.

18. The device of claim 14, wherein the first signal is indicative of the variability of the local basis weight caused by flocs greater than about 8 mm.

19. The device of claim 14, wherein the first signal is indicative of the variability of the local basis weight caused by flocs greater than about 4 mm.

20. The device of claim 14, wherein the first signal is indicative of the variability of the local basis weight caused by flocs greater than a predetermined size.

21. The device of claim 14, further comprising:
   support means for supporting the sheet at a plurality of locations defining an unsupported region between said locations;
   means for applying force to the sheet to deflect the sheet into the unsupported region;
   a force sensor, operatively coupled to the support means, for sensing the force applied to the sheet by the means for applying force, the force sensor operating to generate a fourth signal indicative of the sensed force, wherein the computer computes the strength of the sheet based upon the fourth signal in addition to the first and second signals.

22. The device of claim 21, further comprising means for measuring the distance that the means for applying force deflects the sheet and for generating a fifth signal indicative of the measured deflection, wherein the computer computes the strength of the sheet based upon the fifth signal in addition to the first, second and fourth signals.

23. The device of claim 22, further comprising a tension sensor for measuring the tension in the sheet and generating a sixth signal indicative of the sensed tension, wherein the computer computes the strength of the sheet based upon the sixth signal in addition to the first, second, fourth and fifth signals.

24. A system for determining the strength of a moving paper sheet, the system comprising:
   a light source;
   a light detector disposed to receive light emanating from the light source, the light detector being capable of producing a variable signal when the moving sheet passes between the light source and the light detector, said variable signal being indicative of the intensity of the received light;
   signal processing circuitry operatively coupled to the light detector to receive the signal and produce first and second outputs, wherein the first output is indicative of the flock size of the sheet, and the second output is indicative of the magnitude of variations in local basis weight of the sheet; and
   a computer operatively coupled to the signal processing circuitry to receive the first and second outputs, and wherein the computer is operable to compute sheet strength based upon the outputs and to generate a computer output signal indicative of the computed sheet strength.

25. The system of claim 24, further comprising an average basis weight sensor for producing a basis weight signal indicative of the sensed average sheet basis weight, the basis weight sensor being operatively coupled to the computer, wherein the computer is programmed to compute sheet strength based upon the basis weight signal in addition to the outputs.

26. The system of claim 24, wherein the second output is indicative of the magnitude of variations in the local basis weight of the sheet caused only by flocs greater than a predetermined size.

27. The system of claim 26, wherein the predetermined size is approximately 32 mm.

* * * * *